United States Patent [19]

Cross et al.

[11] Patent Number: 4,788,196

[45] Date of Patent: Nov. 29, 1988

[54] PHENYL PIPERAZINE ANTI-ARRHYTHMIA AGENTS

[75] Inventors: Peter E. Cross, Canterbury; Roger P. Dickinson, Dover, both of England

[73] Assignee: Pfizer Inc., New York, N.Y.

[21] Appl. No.: 39,508

[22] Filed: Apr. 17, 1987

[30] Foreign Application Priority Data

Apr. 19, 1986 [GB] United Kingdom ............... 8609630

[51] Int. Cl.$^4$ ................. A61K 31/495; A61K 31/415; A61K 31/44; C07D 401/02

[52] U.S. Cl. ..................................... 514/252; 544/360; 544/370

[58] Field of Search ................. 544/360, 370; 514/252

[56] References Cited

U.S. PATENT DOCUMENTS

| | | | |
|---|---|---|---|
| 2,543,972 | 3/1951 | Hultquist et al. | 544/360 |
| 2,562,036 | 7/1951 | Hultquist et al. | 544/360 |
| 2,606,906 | 8/1952 | Hultquist et al. | 544/360 |
| 2,663,706 | 12/1953 | Conroy et al. | 544/360 |
| 3,306,903 | 2/1967 | Jain et al. | 260/268 |
| 4,255,575 | 3/1981 | Griesar et al. | 544/394 |
| 4,287,195 | 9/1981 | Heeres et al. | 424/250 |
| 4,544,654 | 10/1985 | Davey et al. | 544/391 |
| 4,569,801 | 2/1986 | Molloy et al. | 514/605 |
| 4,596,827 | 6/1986 | Molloy et al. | 514/605 |
| 4,613,598 | 9/1986 | Fukami et al. | 544/360 |
| 4,639,524 | 1/1987 | Desaiet et al. | 546/229 |
| 4,721,717 | 1/1988 | Friebe et al. | 544/312 |

FOREIGN PATENT DOCUMENTS 233051  8/1987  European Pat. Off. ............ 544/360

OTHER PUBLICATIONS

Galstakhova et al., CA68-87272r (1968).
Feit, CA70-57342n (1969).
Yang et al., CA97-72386f (1982).
Otsuka Pharm. Co Ltd., CA99-937429 (1983).
Knagarajan et al. "Nitroimidazoles: Part VII-I-(Alkyl-5-nitroimidazol-2-yl)-aza(diaza, oxaza)cycloalkanes, in J. Chem. 21B, 949,1982.
Jain et al. "Compounds Acting on the Central Nervous System.
VII, Studies in 1-Pyridyl-4-Substituted Piperazines, A New Class of Anticonvulsants, J. Med. Chem., 10, 312,1967.

Primary Examiner—Donald G. Daus
Assistant Examiner—Cecilia Shen
Attorney, Agent, or Firm—Peter C. Richardson; Paul H. Ginsburg; Robert F. Sheyka

[57] ABSTRACT

A series of pyridyl or imidazolyl substituted phenyl piperazines having utility as anti-arrhythmic agents is disclosed.

10 Claims, No Drawings

PHENYL PIPERAZINE ANTI-ARRHYTHMIA AGENTS

BACKGROUND OF THE INVENTION

This invention relates to certain phenyl-piperazine derivatives which are anti-arrhythmia agents useful for the treatment of cardiac conditions.

The compounds of the invention prolong the duration of the action potential in cardiac muscle and conducting tissue, and thereby increase refractoriness to premature stimuli. Thus, they are Class III anti-arrhythmic agents according to the classification of Vaughan Williams (Anti-Arrhythmic Action, E. M. Vaughan Williams, Academic Press, 1980). They are effective in atria, ventricles and conducting tissue both in vitro and in vivo and are therefore useful for the prevention and treatment of a wide variety of ventricular and supraventricular arrhythmias including atrial and ventricular fibrillation. Because they do not alter the speed at which impulses are conducted, they have less propensity than current drugs (mostly Class I) to precipitate or aggravate arrhythmias, and they also produce less neurological side effects. Some of the compounds also have positive inotropic activity and therefore are particularly beneficial in patients with impaired cardiac pump function.

SUMMARY OF THE INVENTION

Thus the invention provides phenyl-piperazine derivatives of the formula:

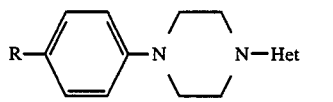

(I)

and their pharmaceutically acceptable salts, wherein
R is $R^3SO_2NH-$, $R^3CONH-$, or $R^1R^2NSO_2-$ or $R^1R^2NCO-$;
$R^1$ and $R^2$ are each independently H or $C_1-C_4$ alkyl;
$R^3$ is $C_1-C_4$ alkyl, $C_3-C_7$ cycloalkyl or $NR^1R^2$; and
Het is 2, 3 or 4-pyridyl optionally substituted by one or more substituents each independently selected from $C_1-C_4$ alkyl and $NH_2$, or 2-imidazolyl optionally substituted by one or more $C_1-C_4$ alkyl groups.

The pharmaceutically acceptable salts of the compounds of the formula (I) include acid addition salts formed from acids which form non-toxic salts such as the hydrochloride, hydrobromide, hydroiodide, sulphate or bisulphate, phosphate or hydrogen phosphate, acetate, maleate, fumarate, lactate, tartrate, citrate, gluconate, benzoate, methanesulphonate, benzenesulphonate and p-toluenesulphonate salts. Some of the compounds, e.g. those in which R is $R^3SO_2NH-$, may also form metal salts, particularly alkaline earth and alkali metal salts. Examples include the sodium and potassium salts.

The invention also includes novel compounds of the formula (I) wherein Het is 2, 3 or 4-pyridyl, or an N-oxide thereof, substituted by $NO_2$, and wherein Het is 2, 3 or 4-pyridyl substituted by $-CONHNH_2$ or $-NHCO_2$ ($C_1-C_4$ alkyl). Such compounds are useful synthetic intermediates for preparation of compounds of the formula (I) wherein Het is amino-substituted pyridyl.

Preferred compounds of the invention are those compounds of formula (I) wherein R is $R^3SO_2NH-$, particularly where $R^3$ is $C_1-C_4$ alkyl; $CH_3SO_2NH-$ being especially preferred. Het is preferably 2- or 4-pyridyl optionally substituted by $CH_3$ or $NH_2$. In particular Het is preferably 4-pyridyl, 2-methyl-4-pyridyl or 4-amino-2-pyridyl. Thus preferred compounds of the invention are those wherein R is $CH_3SO_2NH-$ and Het is 4-pyridyl, 2-methyl-4-pyridyl or 4-amino-2-pyridyl.

DETAILED DESCRIPTION OF THE INVENTION

The compounds of the formula (I) can be prepared by a number of different processes according to the invention as follows:

In one process, compounds of the formula (I) wherein R is $R^3SO_2NH-$ or $R^3CONH-$ are prepared from a compound of the formula:

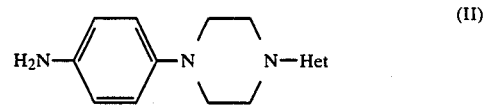

(II)

wherein Het is as previously defined by:

(a) reacting with a sulphonyl chloride of the formula $R^4SO_2Cl$ or a sulphonic anhydride of the formula $(R^4SO_2)_2O$ wherein $R^4$ is $C_1-C_4$ alkyl or $C_3-C_7$ cycloalkyl, to give compounds of the formula (I) wherein R is $R^3SO_2NH-$ and $R^3$ is as defined above for $R^4$. The reaction is typically achieved by stirring the reactants together in a solvent at room temperature for several hours. When a sulphonyl chloride is used the reaction is generally performed in pyridine but with a sulphonic anhydride methylene chloride is a more suitable solvent.

(b) Reacting with a sulphamoyl chloride of the formula $R^1R^2NSO_2Cl$ wherein one or both of $R^1$ and $R^2$ is $C_1-C_4$ alkyl, to give compounds of the formula (I) wherein R is $R^3SO_2NH-$ and $R^3$ is $NR^1R^2$.

(c) Reacting with $H_2NSO_2NH_2$, for example by refluxing in dioxan, to give compounds of the formula (I) wherein R is $R^3SO_2NH-$ and $R^3$ is $NH_2$.

(d) Reacting with an acyl halide of the formula $R^4COCl$ or anhydride of the formula $(R^4CO)_2O$ wherein $R^4$ is as previously defined in (a) above, to give compounds of the formula (I) wherein R is $R^3CONH-$ and $R^3$ is as defined for $R^4$.

(e) Reacting with a $C_1-C_4$ alkyl isocyanate, for example by stirring the reactants together in N,N-dimethylformamide at room temperature for several hours, to give compounds of the formula (I) wherein R is $R^3CONH-$ and $R^3$ is $NH(C_1-C_4$ alkyl).

(f) Reacting with a compound of the formula ($C_1-C_4$ alkyl)$_2$NCOCl to give compounds of the formula (I) wherein R is $R^1R^2NCONH-$ and $R^1$ and $R^2$ are each $C_1-C_4$ alkyl, or (g) Reacting with an alkali metal cyanate under aqueous acidic conditions to give compounds of the formula (I) wherein R is $H_2NCONH-$.

The starting materials of formula (II) are prepared starting with a 4-halonitrobenzene (III) and the appropriate 4-heterocyclyl-piperazine (IV) as shown in the following reaction scheme wherein X is halo, preferably fluoro or chloro:

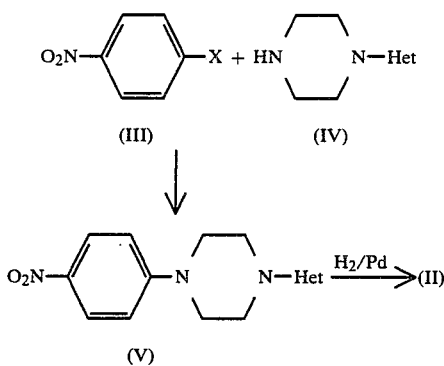

(III)  (IV)

↓

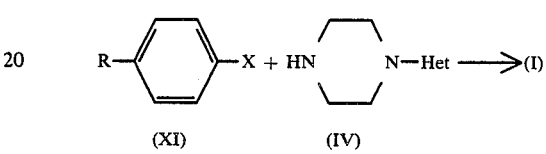

(V)

The coupling reaction is typically achieved by heating the reactants in an inert organic solvent, for example by refluxing in N,N-dimethylformamide, in the presence of sodium bicarbonate, for a period of 3 or 4 hours. The product (V) is then reduced, for example by catalytic hydrogenation using palladium on charcoal, to yield the 4-aminophenylpiperazine (II).

As an alternative process, the starting materials of formula (II) wherein Het is imidazolyl or substituted imidazolyl are prepared from a 4-substituted-phenylpiperazine (VI) as shown in the following reaction scheme wherein $R^8$ is H or $C_1$–$C_4$ alkyl, $R^9$ is $C_1$–$C_4$ alkyl each $R^{10}$ is independently H or $C_1$–$C_4$ alkyl, $R^{11}$ is a $C_1$–$C_4$ alkyl or the two groups $R^{11}$ are joined to form a $C_2$–$C_3$ alkylene chain and Q is halo especially iodo.

ple by reaction with an alkyl halide or dialkyl sulphate, to give the isothiouronium salt (VIII). This may then either be reacted with an aminoacetal to yield a guanidine which is cyclised by treatment with aqueous acid to yield the product (IX), or alternatively reaction with propargylamine yields the methyl-substituted product (X) directly.

In either case the product is reduced, for example by catalytic hydrogenation over palladium on charcoal catalyst, to yield the 4-amino starting material of formula (II) wherein Het is an imidazolyl or substituted imidazolyl group as shown in (IX) or (X).

In a further process, compounds of the formula (I) may be prepared by reaction of a 4-heterocyclylpiperazine (IV) with a 4-substituted-halobenzene (XI) according to the following reaction scheme:

$$R-\text{C}_6\text{H}_4-X + HN\hspace{-1mm}\diagdown\hspace{-1mm}\diagup N-\text{Het} \longrightarrow (I)$$

(XI)  (IV)

wherein R, X and Het are as previously defined.

This route is particularly useful for compounds wherein R is or $R^1R^2NSO_2$— or $R^1R^2NCO$—. The reaction is typically performed by heating the reactants in equimolar proportions in an organic solvent, for example, N,N-dimethylformamide or N-methylpyrrolidone, in the presence of an acid binding agent, for exam-

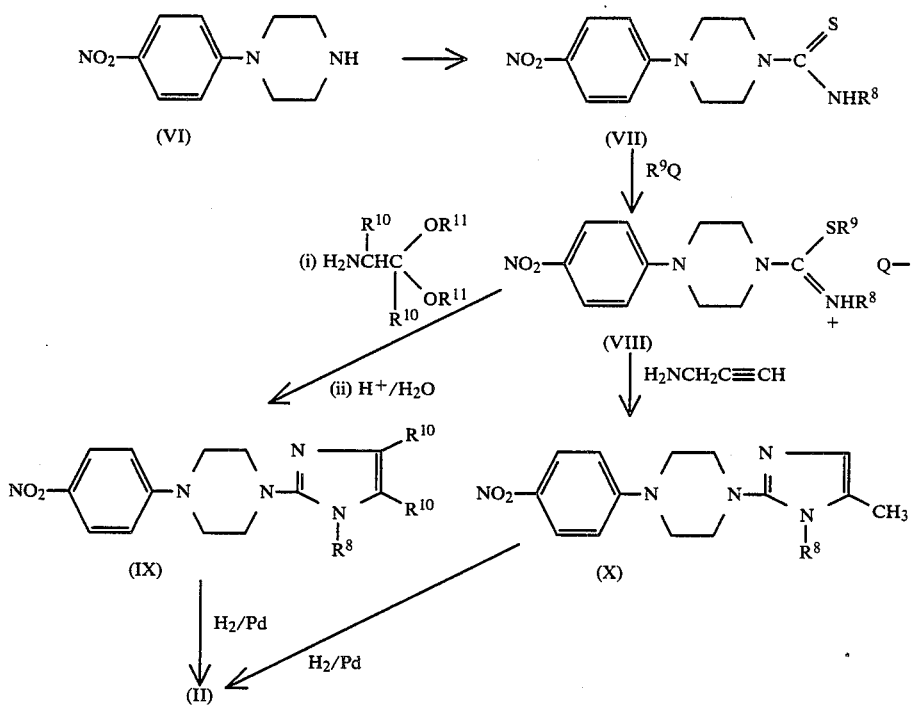

In the first step of this route, the phenylpiperazine (VI) is reacted with a $C_1$–$C_4$ alkyl isothiocyanate in a reaction-inert organic solvent e.g. dichloromethane, at room temperature to yield the thiourea (VII) wherein $R^8$ is $C_1$–$C_4$ alkyl. Alternatively the phenylpiperazine (VI) is heated with a thiocyanate salt, e.g. ammonium thiocyanate under acidic conditions to give the thiourea (VII) wherein $R^8$ is H. This is then alkylated, for example potassium carbonate. A temperature of from 100° C. up to the reflux temperature of the solvent may be used and under these conditions the reaction is generally substantially complete within 24 hours and the product is then isolated and purified by conventional procedures.

In an alternative process for the preparation of compounds of the formula (I) wherein Het is pyridyl or alkyl-substituted pyridyl, a 4-phenyl-piperazine (XII) is reacted with a halo-pyridine (XIII) according to the following reaction scheme:

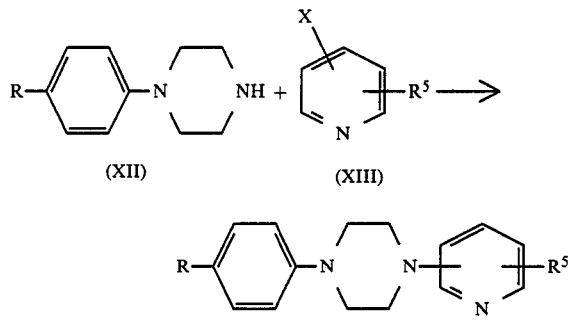

wherein R is as previously defined, X is halo, preferably chloro or bromo and $R^5$ is H or $C_1$–$C_4$ alkyl. The reaction is typically achieved by heating the reactants in equimolar proportions in a reaction-inert organic solvent in the presence of a base.

In the case where Het is amino-substituted pyridyl, the desired compounds of formula (I) are best prepared by reduction of a compound of the formula:

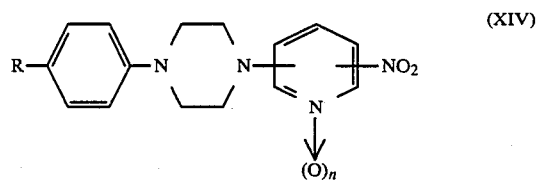

wherein R is as previously defined and n is 0 or 1.

The reduction of the nitro group and, if present, the N-oxide, is achieved by conventional methods, for example by catalytic hydrogenation over palladium on charcoal catalyst.

The nitro intermediates of formula (XIV) may be prepared by the methods described above starting with the appropriate nitro-pyridine or nitro-pyridine-N-oxide. Thus for example the procedure outlined under 3 above may be employed reacting the 4-phenyl-piperazine (XII) with a chloro-nitro-pyridine-N-oxide to give the compound of formula (XIV) wherein n is 1.

In a further process, compounds of the formula (I) wherein R is $R^1R^2NCO$— may be prepared from a compound of the formula:

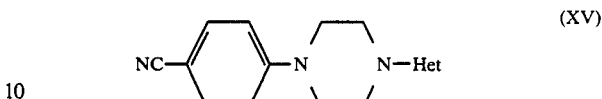

either by mild acid hydrolysis, or base hydrolysis optionally in the presence of hydrogen peroxide, to give the corresponding compound wherein R is $H_2NCO$—; or alternatively by more vigorous acid or base hydrolysis to give the 4-carboxylic acid, followed by conversion to the acid chloride or imidazolide and then reaction with an amine of the formula (wherein one or both of $R^1$ and $R^2$ is $C_1$–$C_4$ alkyl) to give the corresponding compounds of the formula (I) wherein R is $R^1R^2NCO$—.

The starting materials of formula (XV) may be prepared by reaction of a 4-halobenzonitrile with a compound of the formula (IV) in a similar manner to that described above for the compounds of formula (II).

In a further process for preparing compounds wherein Het is amino-substituted pyridyl, the desired compounds of formula (I) are prepared by hydrolysing a compound of the formula:

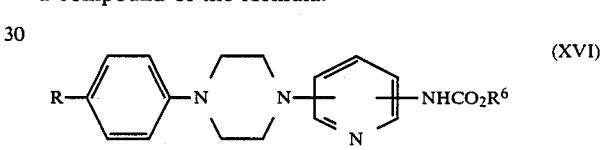

wherein $R^6$ is $C_1$–$C_4$ alkyl.

The reaction is readily achieved by acid or base hydrolysis in an aqueous solvent. For example the reaction may be achieved by heating the compound of formula (XVI) in aqueous sodium hydroxide under reflux for several hours. The solution is neutralised and extracted with an organic solvent to recover the desired product of formula (I).

The starting materials of formula (XVI) are prepared starting from the appropriate halo-pyridine carbohydrazide (XVII) by the methods already described, for example the following route may be used wherein X is halo, $R^6$ is $C_1$–$C_4$ alkyl and $R^7$ is either a group as previously defined for R or is $NO_2$:

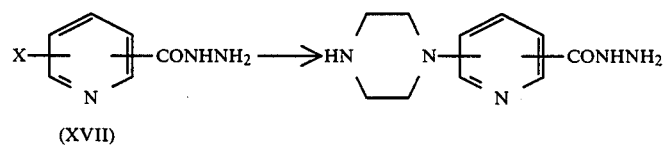

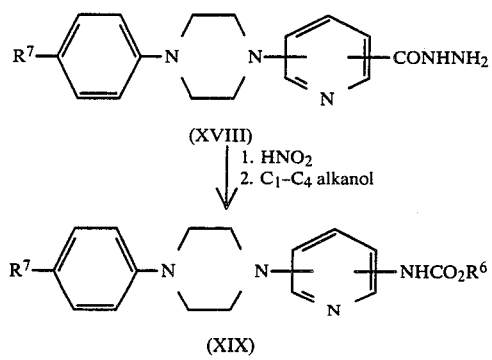

(XVIII)

↓ 1. $HNO_2$
2. $C_1-C_4$ alkanol (XIX)

The carbohydrazide intermediate (XVIII) is treated with nitrous acid followed by heating in a lower alkanol solvent to yield the carbamate (XIX) (Curtius reaction). In the case where $R^7$ is $NO_2$, the product is then hydrogenated to generate the 4-amino compound which is further reacted as described under process 1 above to give the required compound of formula (XVI). For example reaction with methanesulphonyl chloride in pyridine gives the compound of formula (XVI) wherein R is $CH_3SO_2NH-$.

All of the above reactions are conventional and appropriate reagents and reaction conditions for their performance and procedures for isolating the desired products will be well known to those skilled in the art in accordance with literature precedents and by reference to the Examples hereto.

Pharmaceutically acceptable salts are readily prepared by mixing solutions containing equimolar amounts of the free base and the desired acid. The salt generally precipitates from solution or is recovered by evaporation of the solvent.

The biological activity of the compounds of the invention is assessed by measuring the effect of the compounds on atrial refractoriness. In this test guinea pig right hemiatria are mounted in a bath containing physiological salt solution, with one end connected to a force transducer. The tissues are stimulated at 1 Hz using field electrodes. Effective refractory period (ERP) is measured by introducing premature stimuli ($S_2$) after every 8th basic stimulus ($S_1$). The $S_1S_2$ coupling interval is gradually increased until $S_2$ reproducibly elicits a propagated response. This is defined as the ERP. The test compound is then added to the bath and the concentration of compound required to increase ERP by 25% is determined ($ED_{25}$). ERP is also measured in guinea pig right papillary muscles incubated in physiological saline solution. Muscles are stimulated at one end using bipolar electrodes and the propagated electrogram is recorded at the opposite end via a unipolar surface electrode. ERP is determined as above using the extrastimulus technique. Conduction time is obtained from a digital storage oscilloscope by measuring the interval between the stimulus artefact and the peak of the electrogram (i.e. the time required for the impulse to travel along the length of the muscle).

Atrial and vetricular ERP's are also measured in anaesthetised or conscious dogs by the extrastimulus technique whilst the atrium or right ventricle is being paced at a constant rate.

For human use the compounds of the formula (I) can be administered alone but will generally be administered in admixture with a pharmaceutical carrier selected with regard to the intended route of administration and standard pharmaceutical practice. They can be administered both to patients suffering from arrhythmias and also prophylactically to those likely to develop arrhythmias. For example they may be administered orally in the form of tablets containing such excipients as starch or lactose, or in capsules either alone or in admixture with excipients, or in the form of elixirs or suspensions containing flavouring or colouring agents. They may be injected parenterally, for example, intravenously, intramuscularly or subcutaneously. For parenteral administration, they are best used in the form of a sterile aqueous solution which may contain other solutes, for example, enough salts or glucose to make the solution isotonic with blood.

For administraticn to man in the curative or prophylactic treatment of cardiac conditions such as ventricular and supraventricular arrhythmias, including atrial and ventricular fibrillation, it is expected that oral dosages of the compounds of the invention will be in the range from 1 to 75 mg daily, taken in up to 4 divided doses per day, for an average adult patient (70 kg). Thus for a typical adult patient, individual tablets or capsules might contain 1 to 25 mg of active compound, in a suitable pharmaceutically acceptable vehicle or carrier. Dosages for intravenous administration would be expected to be within the range 0.5 to 10 mg per single dose as required. A severe cardiac arrhythmia is preferably treated by the i.v. route in order to effect a rapid conversion to the normal rhythm. Variations on these dosages may occur depending on the weight and condition of the subject being treated as will be determined by the medical practitioner.

Thus the present invention provides a pharmaceutical composition comprising a compound of the formula (I) as defined above or pharmaceutically acceptable salt thereof, together with a pharmaceutically acceptable diluent or carrier.

The invention also provides a method of preventing or reducing cardiac arrhythmias in a human being, which comprises administering to said human an effective amount of a compound of formula (I) or pharmaceutically acceptable salt thereof, or a pharmaceutical composition as defined above.

The invention yet further provides a compound of the formula (I) or pharmaceutically acceptable salt thereof, for use as an anti-arrhythmia agent.

The invention also provides the use of a compound of the formula (I), or a pharmaceutically acceptable salt thereof, for the manufacture of a medicament for the prevention or reduction of cardiac arrhythmias.

The preparation of the compounds of the invention is further illustrated by the following Examples:

EXAMPLE 1

N-{4-[4-(4-Pyridyl)piperazin-1-yl]phenyl}methanesulfonamide (i) 1-(4-Nitrophenyl)-4-(4-pyridyl)piperazine A mixture of 4-fluoronitrobenzene (7.05 g), 4-pyridylpiperazine (8.15 g), anhydrous sodium bicarbonate (10.0 g) and dry N,N-dimethylformamide (100 ml) was heated under reflux with stirring for 3 hours and then cooled and poured into water. The solid was filtered off, washed with water and crystallised from ethanol to give 1-(4-nitrophenyl)-4-(4-pyridyl)piperazine (7.34 g), m.p. 213°–216° C. Further recrystallisation raised the m.p. to 219°–221° C. Found: C,63.76; H,5.85; N,19.96. $C_{15}H_{16}N_4O_2$ requires: C,63.36; H,5.67; N,19.71%.

(ii) 1-(4-Aminophenyl)-4-(4-pyridyl)piperazine

A mixture of 1-(4-nitrophenyl)-4-(4-pyridyl)piperazine (2.07 g) in ethanol (100 ml) was hydrogenated at room temperature under a pressure of 2 bars in the presence of 10% palladium on charcoal (0.25 g). When reduction was complete, the catalyst was filtered off and the filtrate was evaporated. The residue was crystallised from methanol/ethyl acetate to give 1-(4-aminophenyl)-4-(4-pyridyl)piperazine (1.08 g), m.p. 210°–211° C. Found: C,70.47; H,7.07; N,21.56. $C_{15}H_{18}N_4$ requires: C,70.83; H,7.13; N,22.03%.

(iii) N-{4-[4-(4-Pyridyl)piperazin-1-yl]phenyl}methanesulphonamide

Methanesulphonyl chloride (0.50 g) was added dropwise to a stirred solution of 1-(4-aminophenyl)-4-(4-pyridyl)piperazine (1.00 g) in dry pyridine (10 ml) at room temperature. The mixture was stirred at room temperature for 20 hours and then evaporated. The residue was dissolved in water and the solution was basified with sodium bicarbonate solution and allowed to stand for 2 hours. The solid was filtered off, washed with water, dried and crystallised from methanol/ethyl acetate to give the title compound (0.55 g), m.p. 230°–232° C. Found: C,57.80; H,6.07; N,16.89. $C_{16}H_{20}N_4O_2S$ requires: C,57.81; H,6.06; N,16.85%.

EXAMPLE 2

N-{4-[4-(2-Methylpyrid-4-yl)piperazin-1-yl]phenyl}methanesulphonamide (i) 1-(2-Methylpyrid-4-yl)piperazine A mixture of 4-chloro-2-methylpyridine nitrate (5.00 g), piperazine (9.00 g), anhydrous sodium bicarbonate (6.60 g) and amyl alcohol (60 ml) was heated under reflux for 18 hours. The mixture was cooled and water was added to dissolve inorganic material. The organic layer was washed four times with brine and all the aqueous extracts were combined and extracted with ethyl acetate. The organic layers were combined, dried over sodium sulphate and evaporated. The residue was crystallised from ethyl acetate/hexane to give 1-(2-methylpyrid-4-yl)piperazine (2.80 g), m.p. 93°–94° C.

(ii) 1-(2-Methylpyrid-4-yl)-4-(4-nitrophenyl)piperazine

Treatment of 1-(2-methylpyrid-4-yl)piperazine with 4-fluoronitrobenzene by the method of Example 1(i) gave 1-(2-methylpyrid-4-yl)-4-(4-nitrophenyl)piperazine, m.p. 150°–151° C. (from ethyl acetate). Found: C,64.44; H,6.19; N,18.80. $C_{16}H_{18}N_4O_2$. Requires: C,64.41; H,6.08; N,18.78%.

(iii) 1-(4-Aminophenyl)-4-(2-methylpyrid-4-yl)piperazine

Reduction of 1-(2-methylpyrid-4-yl)-4-(4-nitrophenyl)piperazine by the method of Example 1(ii) gave 1-(4-aminophenyl)-4-(2-methylpyrid-4-yl)piperazine, m.p. 155°–156° C. (from ethyl acetate/hexane).

(iv) N-{4-[4-(2-Methylpyrid-4-yl)piperazin-1-yl]phenyl}methanesulphonamide

Treatment of 1-(4-aminophenyl)-4-(2-methylpyrid-4-yl)piperazine with methanesulphonyl chloride by the method of Example 1(iii) gave the title compound, m.p. 184°–185° C. (from ethanol/water). Found: C,58.62; H,6.34; N,15.85. $C_{17}H_{22}N_4O_2S$ requires: C,58.93; H,6.40; N,16.17%.

EXAMPLE 3

1,1-Dimethyl-3-{[4-(4-pyridyl)piperazin-1-yl]phenyl} sulphamide

N,N-Dimethylsulphamoyl chloride (0.12 g) was added to a stirred solution of 1-(4-aminophenyl)-4-(4-pyridyl)piperazine (0.20 g) in dry pyridine (6 ml) and the mixture was stirred for 18 hours and then evaporated. The residue was dissolved in water and the solution was basified with sodium bicarbonate solution. The resulting mixture was extracted several times with dichloromethane and the combined extracts were washed with water and dried over sodium sulphate. Evaporation of the solvent gave a solid which was chromatographed on silica gel. Elution with dichloromethane/methanol (50:1) first gave some impurity followed by pure product. The product containing fractions were combined, evaporated and the solid was crystallised from methanol/ethyl acetate to give the title compound (0.12 g), m.p. 209°–212° C. Found: C,55.92; H,6.53; N,19.17. $C_{17}H_{23}N_5O_2S$ requires: C,56.48; H,6.41; N,19.38%.

EXAMPLE 4

1-Methyl-3-{4-[4-(4-pyridyl)piperazin-1-yl]phenyl}urea

Methyl isocyanate (0.18 g) was added to a stirred solution of 1-(4-aminophenyl)-4-(4-pyridyl)piperazine (0.51 g) in dry N,N-dimethylformamide (5 ml). The resulting mixture was stirred for 3 hours, diluted with a few ml. of ethanol and filtered. The solid was crystallised from methanol to give the title compound (0.33 g), m.p. 258°–260° C. Found: C,65.46; H,6.83; N,22.25. $C_{17}H_{21}N_5O$ requires: C,65.57; H,6.80; N,22.49%.

EXAMPLE 5

N-{4-[4-(1-Methylimidazol-2-yl)piperazin-1-yl]phenyl} methanesulphonamide (i) N-Methyl-4-(4-nitrophenyl)piperazin-1-ylcarbothioamide A solution of methyl isothiocyanate (3.66 g) in dry dichloromethane (20 ml) was added dropwise to a stirred solution cf 1-(4-nitrophenyl)piperazine (10.36 g) in dry dichloromethane (90 ml). The mixture was stirred for 1 hour at room temperature, allowed to stand for 18 hours and then filtered to give N-methyl-4-(4-nitrophenyl)piperazin-1-ylcarbothioamide (12.5 g), m.p. 186°–187° C. (from dichloromethane containing a trace of methanol). Found: C,51.24; H,5.80; N,19.96. $C_{12}H_{16}N_4O_2S$ requires: C,51.41; H,5.75; N,19.99%.

(ii)
N-Methyl-4-(4-nitrophenyl)piperazin-1-ylcarboximidothioic acid methyl ester hydroidide A solution of methyl iodide (6.80 g) in methanol (10 ml) was added dropwise to a stirred suspension of N-methyl-4-(4-nitrophenyl)piperazin-1-ylcarbothioamide (11.80 g) in methanol 120 ml. The mixture was stirred for 48 hours and then a further 6.80 g of methyl iodide was added. The mixture was heated under reflux for 3 hours and then cooled and filtered. The solid was washed with a little methanol and then dried to give N-methyl-4-(4-nitrophenyl)piperazin-1-ylcarboximidothioic acid methyl ester hydroidide (16.50 g), m.p. 178°–179° C. Found: C,37.32; H,4.44; N,13.22. $C_{13}H_{18}N_4O_2S.HI$ requires: C,36.97; H,4.53; N,13.27%.

(iii)
1-(1-Methylimidazol-2-yl)-4-(4-nitrophenyl)piperazine

Aminoacetaldehyde diethyl acetal (1.47 g) was added over 5 minutes to a stirred suspension of N-methyl-4-(4-nitrophenyl)piperazin-1-ylcarboximidothioic acid methyl ester hydroiodide (4.22 g) in pyridine (25 ml). The resulting solution was stirred at 105° C. for 5 hours and then evaporated. The residue was dissolved in 2N hydrochloric acid (60 ml) and the solution was heated under reflux for 1½ hours and then evaporated. The residue was dissolved in water and the solution was basified with sodium bicarbonate. The solid was filtered off, washed with water, dried and then chromatographed on silica gel. The column was eluted with ethyl acetate followed by ethyl acetate/methanol (50:1) to give 1-(1-methylimidazol-2-yl)-4-(4-nitrophenyl)piperazine (1.60 g), m.p. 193°–194° C. (from ethyl acetate). Found: C,58.81; H,6.04; N,24.41. $C_{14}H_{17}N_5O_2$ requires: C,58.52; H,5.97; N,24.38%.

(iv)
1-(4-Aminophenyl)-4-(1-methylimidazol-2-yl)piperazine

Reduction of 1-(1-methylimidazol-2-yl)-4-(4-nitrophenyl)piperazine by the method of Example 1(ii) gave 1-(4-aminophenyl)-4-(1-methylimidazol-2-yl)piperazine as a gum which was used directly in the next stage.

(v)
N-{4-[4-(1-Methylimidazol-2-yl)piperazin-1-yl]phenyl}methanesulphonamide

Treatment of 1-(4-aminophenyl)-4-(1-methylimidazol-2-yl)piperazine with methanesulphonyl chloride by the method of Example 1(iii) gave a solid which was purified by chromatography on silica gel. The column was eluted with ethyl acetate followed by ethyl acetate/methanol (15:1). The product containing fractions were evaporated and the solid was crystallised from methanol/ethyl acetate to give the title compound, m.p. 211°–212° C. Found: C,53.36; H,6.64; N,20.74. $C_{15}H_{21}N_5O_2S$ requires: C,53.71; H,6.31; N,20.88%.

EXAMPLE 6

N-{4-[4-(1,5-Dimethylimidazol-2-yl)piperazin-1-yl]phenyl}methanesulphonamide (i)
1-(1,5-Dimethylimidazol-2-yl)-4-(4-nitrophenyl)piperazine Propargylamine (2.75 g) was added over 2 minutes to a stirred suspension of N-methyl-4-(4-nitrophenyl)piperazin-1-ylcarboximidothioic acid methyl ester hydroidide (the product of Example 5(ii)) (4.22 g) in pyridine (25 ml) at room temperature. The resulting solution was stirred at 105° C. for 2 hours and then evaporated. The residue was dissolved in water and the solution was basified with sodium bicarbonate. The solid was filtered off, washed with water, dried and then chromatographed on silica gel. The column was eluted with ethyl acetate followed by ethyl acetate/methanol (5:1). Some impurity was eluted initially followed by a solid which was crystallised from methanol/ethyl acetate to give 1-(1,5-dimethylimidazol-2-yl)-4-(4-nitrophenyl)piperazine (1.80 g), m.p. 204°–205° C. Found: C,59.58; H,6.36; N,22.89. $C_{15}H_{19}N_5O_2$ requires: C,59.78; H,6.35; N,23.24%.

(ii)
1-(4-Aminophenyl)-4-(1,5-dimethylimidazol-2-yl)piperazine

Reduction of 1-(1,5-dimethylimidazol-2-yl)-4-(4-nitrophenyl)piperazine by the method of Example 1(ii) gave 1-(4-aminophenyl)-4-(1,5-dimethylimidazol-2-yl)piperazine as a gum which was used directly in the next stage.

(iii)
N-{4-[4-(1,5-Dimethylimidazol-2-yl)piperazin-1-yl]phenyl}methanesulphonamide Treatment of 1-(4-aminophenyl)-4-(1,5-dimethylimidazol-2-yl)piperazine with methanesulphonylchloride followed by chromatography as described in Example 5(v) gave the title compound, m.p. 257° C. (decomp). Found: C,55.00; H,6.70; N,19.55. $C_{16}H_{23}N_5O_2S$ requires: C,54.99; H,6.63; N,20.04%.

EXAMPLE 7

N-{4-[4-(4-Pyridyl)piperazin-1-yl]phenyl}acetamide

A solution of 1-(4-aminophenyl)-4-(4-pyridyl)piperazine (0.33 g) in a mixture of dichloromethane (20 ml) and acetic anhydride (1.5 ml) was allowed to stand overnight and then evaporated. The residue was triturated with 50 ml of 10% sodium carbonate solution, and then the mixture was diluted to 100 ml with water and extracted several times with chloroform. The combined extracts were dried over sodium sulphate, evaporated and the residue crystallised from ethanol to give the title compound (0.15 g), m.p. 244°–247° C. Found: C,68.82; H,6.67; N,18.69. $C_{17}H_{20}N_4O$ requires: C,68.89; H,6.80; N,18.91%.

EXAMPLE 8

N-{4-[4-(4-Pyridyl)piperazin-1-yl]phenyl}urea

A solution of sodium cyanate (0.26 g) in water (30 ml) was added over 10 minutes to a stirred solution of 1-(4-aminophenyl)-4-(4-pyridyl)piperazine (0.50 g) in a mixture of acetic acid (20 ml) and water (30 ml). The solution was stirred for 2 hours, allowed to stand for 18 hours and then evaporated. The residue was triturated with water and filtered. The solid was crystallised from N,N-dimethylformamide to give the title compound (0.27 g), m.p. above 250° C. Found: C,64.17; H,6.42; N,23.32. $C_{16}H_{19}N_5O$ requires: C,64.62; H,6.44; N,23.55%.

EXAMPLE 9

N-{4-[4-(4-Pyridyl)piperazin-1-yl]phenyl}sulphamide

A solution of 1-(4-aminophenyl)-4-(4-pyridyl)piperazine (0.50 g) and sulphamide (1.90 g) in dioxan (30 ml) was heated under reflux for 1 hour and then evaporated. The residue was triturated with water and the mixture was filtered. The solid was crystallised from a mixture of N,N-dimethylformamide and water to give the title compound (0.11 g), m.p. 216°–219° C. Found: C,54.03; H,5.59; N,20.68. $C_{15}H_{19}N_5O_2S$ requires: C,54.05; H,5.75; N,21.01%.

EXAMPLE 10

N-{4-[4-(3-Methylpyrid-4-yl)piperazin-1-yl]phenyl}methanesulphonamide (i) 1-(3-Methylpyrid-4-yl)-4-(4-nitrophenyl)piperazine Treatment of 1-(3-methylpyrid-4-yl)piperazine with 4-fluoronitrobenzene by the method of Example 1(i) gave the title compound, m.p. 107°–109° C. Found: C,63.98; H,6.12; N,19.21. $C_{16}H_{18}N_4O_2$ requires: C,64.41; H,6.08; N,18.78%.

(ii)
1-(4-Aminophenyl)-4-(3-methylpyrid-4-yl)piperazine

Reduction of the product from (i) above by the method of Example 1(ii) gave the title compound, m.p. 163°–164.5° C. Found: C,71.31; H,7.59; N,20.61. $C_{16}H_{20}N_4$ requires: C,71.61; H,7.51; N,20.88%.

(iii)
N-{4-[4-(3-Methylpyrid-4-yl)piperazin-1-yl]}phenyl methanesulphonamide

Treatment of the product from (ii) above with methanesulphonyl chloride by the method of Example 1(iii) gave the title compound, m.p. 230°–232° C. Found: C,58.82; H,6.32; N,16.06. $C_{17}H_{22}N_4O_2S$ requires: C,58.93; H,6.40; N,16.17%.

EXAMPLE 11

N-{4-[4-(4-Aminopyrid-2-yl)piperazin-1-yl]phenyl}methanesulphonamide (i) 1-Acetyl-4-(4-aminophenyl)piperazine A solution of 1-acetyl-4-(4-nitrophenyl)piperazine (28.8 g) in ethanol (400 ml) was hydrogenated at 4 bar in the presence of 10% palladium/carbon (0.5 g) until no further hydrogen was taken up. The catalyst was filtered off and the filtrate was evaporated. The residue was triturated with diethyl ether, filtered and dried to give the title compound (23.8 g), m.p. 142°–144° C.

(ii)
N-[4-(Acetylpiperazin-1-yl)phenyl]methanesulphonamide

Methanesulphonyl chloride (6.30 g) was added dropwise to a stirred solution of the product of (i) above (10.96 g) in dry pyridine (100 ml) at 0° C. The mixture was stirred at room temperature for 18 hours and then evaporated. The residue was triturated with saturated sodium bicarbonate solution and filtered. The residue was washed with water, dried and crystallised from a mixture of methanol and ethyl acetate to give the title compound (9.97 g), m.p. 165°–167° C. Found: C,52.44; H,6.27; N,14.09. $C_{13}H_{19}N_3O_3S$ requires: C,52.50; H,6.44; N,14.13%.

(iii) N-[(4-piperazin-1-yl)phenyl]methanesulphonamide hydrochloride

A solution of the above product (9.60 g) in 5N hydrochloric acid (100 ml) was heated on a steam bath for 1 hour and then evaporated. The residue was crystallised from aqueous ethanol to give the title compound (8.26 g), m.p. 228°–230° C. Found: C,44.54; H,6.29; N,14.00. $C_{11}H_{17}N_3O_2S.HCl. 0.25 H_2O$ requires: C,44.74; H,6.05; N,14.23%.

(iv)
N-{4-[4-(4-Nitropyrid-2-yl)piperazin-1-yl]phenyl}methanesulphonamide

A mixture of the product of (iii) above (1.46 g), 2-chloro-4-nitropyridine (0.79 g) and sodium bicarbonate (1.26 g) in n-butanol (30 ml) were heated under reflux with stirring for 24 hours and then cooled and filtered. The solid was washed with methanol and the combined filtrate and washings were evaporated to give a gum that was chromatographed on silica gel. Elution with dichloromethane, gradually increasing the polarity to dichloromethane/methanol (4:1) gave a mixture of the desired product, together with some N-{4-[4-(2-chloropyrid-4-yl)piperazin-1-yl]phenyl}methanesulphonamide biproduct, as a solid. The solid was crystallised four times from methanol to give pure N-{4-[4-(4-nitropyrid-2-yl)piperazin-1-yl]phenyl}methanesulphonamide (0.36 g), m.p. 182°–183° C. Found: C,50.90; H,5.07; N,18.51. $C_{16}H_{19}N_5O_4S$ requires: C,50.91; H,5.07; N,18.56%.

(v)
N-{4-[4-(4-Aminopyrid-2-yl)piperazin-1-yl]phenyl}methanesulphonamide

A solution of N-{4-[4-(4-nitropyrid-2-yl)piperazin-1-yl]phenyl}methanesulphonamide (100 mg) in methanol (40 ml) was hydrogenated at 3 bar and 22° C. in the presence of 5% palladium on carbon (20 mg) until no more hydrogen was taken up. The catalyst was filtered off and the filtrate was evaporated. The residue was crystallised from aqueous methanol to give the title compound (55 mg), m.p. 225°–227° C. Found: C,55.50; H,6.04; N,19.66. $C_{16}H_{21}N_5O_2S$ requires: C,55.31; H,6.09; N,20.16%.

EXAMPLE 12

N-{4-[4-(4-Aminopyrid-3-yl)piperazin-1-yl]phenyl}methanesulphonamide (i)
N-{4-[4-(4-Nitro-1-oxidopyrid-3-yl)piperazin-1-yl]phenyl}methanesulphonamide A mixture of N-[(4-piperazin-1-yl)phenyl]methanesulphonamide hydrochloride (the product of Example 11, (iii) (0.59 g), 3-chloro-4-nitropyridine-N-oxide (0.35 g) and sodium bicarbonate (0.50 g) in n-butanol (25 ml) was heated at 100° C. with stirring for 1.5 hours and then evaporated. The residue was stirred with water, filtered, and the solid was crystallised from methanol to give the title compound (0.55 g), m.p. 206°–208° C. Found: C,48.77; H,4.91; N,17.52. $C_{16}H_{19}N_5O_5S$ requires: C,48.84; H,4.87; N,17.80%.

(ii) N-{4-[4-(4-Aminopyrid-3-yl)piperazin-1-yl]phenyl}methanesulphonamide

A suspension of the above product (150 mg) in acetic acid (5 ml) was hydrogenated at 2 bar and room temperature in the presence of Raney nickel (30 mg). When no more hydrogen was taken up, the catalyst was filtered off and the solution was evaporated. The residue was chromatographed on silica gel. Elution was commenced with ethyl acetate and the polarity was gradually increased to ethyl acetate/methanol (5:1) to give a solid that was crystallised from aqueous methanol to give the title compound (65 mg), m.p. 246°–248° C. Found: C,55.39; H,6.17; N,19.76. $C_{16}H_{21}N_5O_2S$ requires: C,55.31; H,6.09; N,20.16%.

EXAMPLE 13

N-Methyl-4-[4-(4-pyridyl)piperazin-1-yl]benzenesulphonamide

A mixture of 1-(4-pyridyl)piperazine (0.86 g), N-methyl-4-fluorobenzenesulphonamide (1.00 g) and potassium carbonate (2.00 g) in N-methylpyrrolidone was stirred at 100° C. for 24 hours and then evaporated. The residue was partitioned between dichloromethane and 2N hydrochloric acid. The acid layer was washed with dichloromethane, filtered and made basic with sodium bicarbonate solution. The mixture was extracted several times with chloroform, and the combined extracts were washed with water, dried over magnesium sulphate and evaporated. The residue was crystallised from ethanol/ethyl acetate to give the title compound (0.12 g), m.p. 204°–206° C. Found: C,57.55; H,6.13; N,16.62. $C_{16}H_{20}N_4O_2S$ requires: C,57.81; H,6.06; N,16.85%.

EXAMPLE 14

4-[4-(4-Pyridyl)piperazin-1-yl]benzenesulphonamide

Treatment of 1-(4-pyridyl)piperazine with 4-fluorobenzenesulphonamide according to the method of Example 13 gave the title compound, m.p. 250°–255° C. Found: C,56.35; H,5.64; N,17.49. $C_{15}H_{18}N_4O_2S$ requires: C,56.58; H,5.70; N,17.60%.

EXAMPLE 15

4 [4-(4-Pyridyl)piperazin-1-yl]benzamide (i) 4-[4-(4-Pyridyl)piperazin-1-yl]benzonitrile A mixture of 1-(4-pyridyl)piperazine (4.05 g), 4-fluorobenzonitrile (3.00 g) and potassium carbonate (7.00 g) in N-methylpyrrolidone (25 ml) was heated at 80° C. with stirring for 18 hours. The solvent was then evaporated and the residue was partitioned between dichloromethane and water. The organic layer was washed with water, dried over magnesium sulphate and evaporated. The residue was crystallised from ethanol to give the title compound (1.80 g), m.p. 155°–158° C. Found: C,72.50; H,5.96; N,21.24. $C_{16}H_{16}N_4$ requires: C,72.70; H,6.10; N,21.20%.

(ii) 4-[4-(4-Pyridyl)piperazin-1-yl]benzamide

A solution of sodium hydroxide (1.0 g) in water (5 ml) was added to a solution of the product of (i) above (1.0 g) in ethanol (10 ml), followed by 30% hydrogen peroxide solution (2.5 ml). The mixture was stirred at 50° C. for 1.5 hours, at room temperature for 1 hour and then evaporated. The residue was triturated with water, the mixture was filtered and the solid was crystallised from n-propanol/water to give the title compound (0.28 g), m.p. 327°–330° C. Found: C,68.31; H,6.59; N,19.78. $C_{16}H_{18}N_4O$ requires: C,68.09; H,6.43; N,19.85%.

EXAMPLE 16

N-{4-[4-(2-Pyridyl)piperazin-1-yl]phenyl}methanesulphonamide (i) 1-(4-Nitrophenyl)-4-(2-pyridyl)piperazine Treatment of 1-(2-pyridyl)piperazine with 4-fluoronitrobenzene according to the method of Example (i) gave the title compound, m.p. 187°–188° C.

(ii) 1-(4-Aminophenyl)-4-(2-pyridyl)piperazine

Hydrogenation of the product of (i) above according to the method of Example 1(ii) gave the title compound, m.p. 119°–120° C.

(iii) N-{4-[4-(2-Pyridyl)piperazin-1-yl]phenyl}methanesulphonamide

Treatment of the product of (ii) above with methanesulphonyl chloride according to the method of Example 1(iii) gave the title compound, m.p. 180°–181° C. Found: C,57.61; H,6.02; N,16.81. $C_{16}H_{20}N_4O_2S$ requires: C,57.81; H,6.06; N,16.85%.

EXAMPLE 17

N-{4-[4-(3-Pyridyl)piperazin-1-yl]phenyl}methanesulphonamide (i) 1-(4-Nitrophenyl)-4-(3-pyridyl)piperazine Treatment of 1-(3-pyridyl)piperazine with 4-fluoronitrobenzene according to the method of Example 1(i) gave the title compound, m.p. 180°–182° C. Found: C,63.10; H,5.67; N,19.78. Chd $15H_{16}N_4O_2$ requires: C,63.36; H,5.67; N,19.71%.

(ii) 1-(4-Aminophenyl)-4-(3-pyridyl)piperazine

Hydrogenation of the product of (i) above according to the method of Example 1(ii) gave the title compound that was used directly in the next step.

(iii) N-{4-[4-(3-Pyridyl)piperazin-1-yl]phenyl}methanesulphonamide

Treatment of the product of (ii) above with methanesulphonyl chloride according to the method of Example 1(iii) gave the title compound, m.p. 215°–218° C. Found: C,58.06; H,6.21; N,16.70%. $C_{16}H_{20}N_4O_2S$ requires: C,57.81; H,6.06; N,16.85%.

EXAMPLE 18

N-{4-[4-(2-Aminopyrid-4-yl)piperazin-1-yl]phenyl}methanesulphonamide (i) 4-(1-Piperazinyl)pyridine-2-carboxylic acid hydrazide A mixture of 4-chloropyridine-2-carboxylic acid hydrazide (9.37 g), piperazine (20.0 g) and sodium bicarbonate (15 g) in n-butanol (120 ml) was heated under reflux with stirring for 18 hours and then cooled and filtered. The filtrate was evaporated and the residue was chromatographed on silica gel. Elution with a mixture of chloroform, ethanol and concentrated aqueous ammonia solution (50:50:1) gave the product as a solid (8.10 g), m.p. 212°–217° C. (decomp.).

(ii)
4-[4-(4-Nitrophenyl)piperazin-1-yl]pyridine-2-carboxylic acid hydrazide

A mixture of the product of (i) above (7.76 g), 4-fluoronitrobenzene (5.50 g) and sodium carbonate (4.50 g) in N,N-dimethylformamide (40 ml) was heated at 100° C. with stirring for 4 hours. The mixture was evaporated to about half volume and filtered. The residue was washed with ethanol followed by warm water and then dried to give the title compound. (9.41 g), m.p. 230°-232° C.

(iii)
1-[2-(Ethoxycarbonylamino)pyrid-4-yl]-4-(4-nitrophenyl)piperazine

A solution of sodium nitrite (0.89 g) in water (18 ml) was added dropwise to a stirred suspension of the product of (ii) above (4.00 g) in 2N hydrochloric acid (75 ml). The mixture was stirred at 0° C. for 3 hours and then made basic by the addition of sodium bicarbonate solution. The solid was filtered off, washed with water, dried under vacuum and suspended in ethanol (400 ml). The mixture was heated under reflux for 3 hours and then cooled. The solid was filtered off, washed with ethanol and dried to give the title compound (2.31 g), m.p. 243°-245° C. Found: C,58.34; H,5.53; N,18.73. $C_{18}H_{21}N_5O_4$ requires: C,58.22; H,5.56; N,18.87%.

(iv)
1-[2-(Ethoxycarbonylamino)pyrid-4-yl]-4-4-aminophenyl)piperazine

10% Palladium on carbon (1.0 g) was added portionwise to a stirred suspension of the product of (iii) above (0.42 g) in a 5% solution of formic acid in methanol (85 ml). The mixture was stirred at room temperature for 30 minutes, heated under reflux for 15 minutes and then cooled and filtered. The residue was washed with methanol and the combined filtrate and washings were evaporated to give the crude amine (275 mg) which was used directly in the next stage.

(v)
N-{(4-[4-(2-Ethoxycarbonylaminopyrid-4-yl)piperazin-1yl]phenyl}methanesulphonamide Methanesulphonyl chloride (0.11 g) was added to a stirred solution of the product of (iv) above (0.275 g) in pyridine (4 ml) at 0° C. The mixture was stirred at room temperature for 12 hours and then evaporated. The residue was stirred with saturated sodium bicarbonate solution (5 ml) for 15 minutes and the mixture was filtered. The solid was dried and then chromatographed on silica gel. Elution with dichloromethane/methanol (19:1) first gave some impurity followed by the required product (25 mg) which was used directly in the next stage.

(vi)
N-{4-[4-(2-Aminopyrid-4-yl)piperazin-1-yl]phenyl}methanesulphonamide

A mixture of the product from (v) (18 mg), 40% aqueous sodium hydroxide (1.0 ml) and ethanol (0.1 ml) was heated under reflux for 5 hours. The mixture was cooled, acidified to pH 2 with 2N hydrochloric acid and then basified to pH 8-9 with saturated sodium bicarbonate solution. The mixture was extracted several times with dichloromethane and the combined extracts were dried over sodium sulphate and evaporated. The residue was chromatographed on silica gel. Elution with dichloromethane/methanol (19:1) gave some impurity. Addition of 1% of conc. aqueous ammonia to the eluent then gave the title compound (1.6 mg). NMR (CD$_3$OD), 2.86 (s, 3H, CH$_3$), 3.20 (m, 4H) and 3.40 (m, 4H) piperazine CH$_2$, 5.86 (s, 1H, pyridine 3-H), 6.19 (d, 1H, J=6.3 Hz, pyridine 5-H), 6.88 (d, 2H, J=8.75 Hz) and 7.14 (d, 2H, J=8.75 Hz) phenyl H, 7.63 (d, 1H, J=6.3 Hz, pyridine 6-H).

We claim:
1. A compound of the formula:

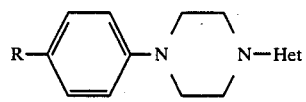

(I)

or a pharmaceutically acceptable salt thereof,
wherein
R is R$^3$SO$_2$NH—, R$^3$CONH—. R$^1$R$^2$NSO$_2$—, or R$^1$R$^2$NCO—;
R$^1$ and R$^2$ are each independently H or C$_1$-C$_4$ alkyl;
R$^3$ is C$_1$-C$_4$ alkyl, C$_3$-C$_7$ cycloalkyl or NR$^1$R$^2$; and
"Het" is 2, 3 or 4-pyridyl optionally substituted by one or more substituents each independently selected from C$_1$-C$_4$ alkyl and NH$_2$; or 2-imidazolyl optionally substituted by one or more C$_1$-C$_4$ alkyl groups.

2. A compound according to claim 1 wherein R is CH$_3$SO$_2$NH.

3. A compound according to claim 1 wherein Het is 2 or 4-pyridyl optionally substituted by CH$_3$ or NH$_2$.

4. A compound according to claim 2 wherein Het is 2 or 4-pyridyl optionally substituted by CH$_3$ or NH$_2$.

5. A compound according to claim 1 wherein R is CH$_3$SO$_2$NH and Het is 4-pyridyl.

6. A compound according to claim 1 wherein R is CH$_3$SO$_2$NH— and Het is 2-methyl-4-pyridyl.

7. A compound according to claim 1 wherein R is CH$_3$SO$_2$NH and Het is 4-amino-2-pyridyl.

8. A pharmaceutical composition comprising a compound of claim 1 in an amount effective to treat cardiac arrhythmias and a pharmaceutically acceptable diluent or carrier.

9. A method of treating cardiac arrhythmias comprising administering to a arrhythmic host in need of such treatment an anti-arrhythmic effective dose of a compound of claim 1 in combination with a pharmaceutically acceptable diluent or carrier.

10. A compound of the formula:

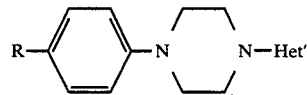

wherein R is as defined in claim 1 and Het' is 2, 3, or 4-pyridyl or an N-oxide thereof substituted by NO$_2$ or wherein Het' is 2, 3 or 4-pyridyl substituted by —CONHNH$_2$ or —NHCO$_2$ (C$_1$-C$_4$ alkyl).

* * * * *